United States Patent
Straussberger

(10) Patent No.: US 6,939,984 B2
(45) Date of Patent: Sep. 6, 2005

(54) PROCESS FOR PREPARING ALKYLCHLOROSILANES FROM THE RESIDUES OF DIRECT SYNTHESIS OF ALKYLCHLORSILANES

(75) Inventor: Herbert Straussberger, Mehring (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 10/981,972

(22) Filed: Nov. 5, 2004

(65) Prior Publication Data

US 2005/0113591 A1 May 26, 2005

(30) Foreign Application Priority Data

Nov. 20, 2003 (DE) ................................. 103 54 262

(51) Int. Cl.$^7$ ............................................... C07F 7/08
(52) U.S. Cl. ...................... 556/466; 556/468; 556/473; 556/477
(58) Field of Search ................................. 556/466, 468, 556/473, 477

(56) References Cited

U.S. PATENT DOCUMENTS

| 2,681,355 A | 6/1954 | Barry et al. |
| 5,877,337 A | 3/1999 | Maufner et al. |
| 2002/0183537 A1 | 12/2002 | Streckel et al. |

FOREIGN PATENT DOCUMENTS

EP  0 635 510  1/1995

*Primary Examiner*—Samuel Barts
(74) *Attorney, Agent, or Firm*—Brooks Kushman P.C.

(57) ABSTRACT

The invention provides a continuous process for preparing alkylchlorosilanes from the residues of direct synthesis of alkylchlorosilanes which comprise liquid constituents with a boiling point of at least 70° C. at 1013 hPa and may also contain solids, with hydrogen chloride, by passing the residues at a temperature not above 200° C. and hydrogen chloride at a temperature higher than the latter into a reactor so that the resultant reaction temperature is from 400° C. to 800° C.

10 Claims, No Drawings

PROCESS FOR PREPARING ALKYLCHLOROSILANES FROM THE RESIDUES OF DIRECT SYNTHESIS OF ALKYLCHLORSILANES

BACKGROUND OF THE INVENTION

1. Field of the Invention

The invention relates to a continuous process for preparing alkylchlorosilanes, in which the residues of direct synthesis of alkylchlorosilanes are cleaved thermally using hydrogen chloride.

2. Background Art

During the direct synthesis of alkylchlorosilanes of the general formula $R_aH_bSiCl_{4-a-b}$, in which a is 1, 2, 3 or 4 and b is 0, 1 or 2, from metallic silicon and alkyl chlorides R—Cl, where R is an alkyl radical, oligosilanes, carbosilanes, siloxanes and high-boiling cracking products are produced as by-products. The residues moreover contain solids from the direct synthesis, which, as fines, are not retained even by cyclones and filters. The solids are composed of silicon, metal chlorides, e.g. $AlCl_3$, metal silicides and soot.

The oligosilanes, in particular the disilanes of the general formula $R_cCl_{6-c}Si_2$, in which c is from 0 to 6, make up the predominant part of these residues. However, silane compounds having more than 2 Si—Si bonds, e.g. trisilanes, may also be present.

U.S. Pat. No. 2,681,355 describes a continuous process in which residues with boiling points above 70° C. from direct synthesis of methylchlorosilanes are reacted with hydrogen chloride at temperatures of from 400 to 900° C. in a tube without internals, giving monomeric silanes. The process proceeds without catalysis and is purely thermal. High proportions of by-products, e.g. carbosilanes and polymers, are formed during this reaction. Solids are also produced via carbonization of the residues on the hot reactor walls.

Published U.S. application 2002/0183537 describes a process for the thermal cleavage of the residues of direct synthesis of alkylchlorosilanes in which the required hydrogen chloride is prepared in the same step of the process from $H_2$ and $Cl_2$. The reactor is of complex structure, and the process is therefore difficult to control. Local overheating can easily occur, promoting the formation of by-products. Chlorinated hydrocarbons and chlorinated alkylchlorosilanes can also be produced.

SUMMARY OF THE INVENTION

An object of the present invention was to provide a process for the preparation of alkylchlorosilanes from the residues of direct synthesis of alkylchlorosilanes which is easy to carry out, and which generates little by-product formation. This and other objects are achieved by introducing alkylchlorosilane process residue into a reactor at a temperature lower than 200° C., and introducing hydrogen chloride at a higher temperature, the reaction temperature in the reactor being from 400° C. to 800° C.

DETAILED DESCRIPTION OF THE PREFERRED EMBODIMENT(S)

The invention thus provides a continuous process for preparing alkylchlorosilanes from the residues of direct synthesis of alkylchlorosilanes, which comprise liquid constituents with a boiling point of at least 70° C. at 1013 hPa and which may also contain solids. The residues are reacted with hydrogen chloride, by passing the residues, at a temperature not above 200° C., and passing hydrogen chloride at a temperature higher than 200° C. into a reactor, and reacting at a temperature from 400 to 800° C.

The process produces useful silanes from residues of direct synthesis of alkylchlorosilanes. It is simple to carry out and can be operated at low pressures. As compared to the process described in U.S. Pat. No. 2,681,355, formation of by-products is reduced, and in particular there is less formation of solid residues on the reactor walls.

It is preferable to prepare alkylchlorosilanes of the above general formula where R is a methyl, ethyl, butyl, or propyl radical, in particular a methyl radical.

The residues of the direct synthesis preferably comprise liquid constituents with a boiling point of at least 80° C., in particular at least 100° C., both measured at 1013 hPa.

The residues are fed into a reactor at a temperature of at most 200° C., preferably at most 180° C., in order to avoid polymerization.

The hydrogen chloride is passed into the reactor in the form of a combined stream or else divided into two or more substreams with different temperatures. The temperature(s) selected for the hydrogen chloride should be sufficiently high so as to provide a reaction temperature of from 400 to 800° C. in the reactor. The heating of the reactants to reaction temperature is therefore, at least in part, the result of direct heat exchange between the reactants. The temperature of the hydrogen chloride is preferably at least 450° C., more preferably at least 500° C., and at most 850° C., more preferably at most 800° C.

The streams of the materials are preferably metered in continuously.

The mixing in the reactor preferably takes place by way of a single- or twin-fluid nozzle. A single-fluid nozzle sprays the preferably liquid residues. A twin-fluid nozzle sprays the preferably liquid residues and the hydrogen chloride, and it is possible here to spray only a portion of the hydrogen chloride, or else the entire amount of hydrogen chloride used.

Preferably, the Si—Si bonds of the di- and oligosilanes present in the residues are cleaved. The molar amount of hydrogen chloride employed should be at least equivalent to that of the Si—Si bonds present in the residue, but not more than 150 times this amount. The molar amount used is preferably greater by a factor of 2 to 60. After the reaction, and after the removal of the alkylchlorosilanes formed, e.g. via condensation, some or all of the excess of hydrogen chloride may be returned to the reactor or passed on to another use.

In order to create isothermic reaction conditions, the reactor, preferably a tubular reactor, most preferably comprises a jacket capable of direct or indirect temperature control up to 800° C. Possible heating methods use high-temperature-resistant fluids, electrical resistance heating, induction heating, or combinations thereof. Direct cooling, e.g. via injection and vaporization of silanes with a boiling point below 100° C., or else regulation of the HCl temperature and, respectively, of the amount of feed of high-boilers are other methods for temperature control.

The reactor is operated at from 400 to 800° C., preferably from 550 to 700° C. The pressure is preferably from 1000 to 10,000 hPa, in particular from 1000 to 3000 hPa.

The length:diameter ratio of the reactor is at least 0.5, preferably at least 5. The reactor may be operated horizontally, and is preferably operated vertically.

The residue and the hydrogen chloride may be metered in counter-currently or co-currently. Where appropriate, for one stream there may be two or more metering points divided over the length of the reactor.

The mixture emerging from the reactor is condensed, e.g. in a quench zone or heat exchanger, and, where appropriate, freed from solids, and can be returned to the alkylchlorosilane mixture produced in the direct synthesis, or else be separated to give pure substances in a separate procedure.

If the residues comprise fine-grained solids, a positive auxiliary effect of the heat treatment is sintering of the solid particles, which are then in suspended form in the condensed product. This method can convert solids which are difficult to filter, for example those possibly dispersed in the form of colloids, into fractions that can be filtered.

EXAMPLE

Unless otherwise stated, all data concerning amounts and percentages are based on weight, and all pressures are 0.10 MPa (abs.), and all temperatures are 20° C.

A high-boiling residue from the direct synthesis of methyl chlorosilanes was used, its composition according to GC being: 42% of disilanes (mixture of 1,1,1,3,3,3-hexamethyldisilane, 1-chloropentamethyldisilane, 1,3-dichlorotetramethyldisilane, 1,1-dichlorotetramethyldisilane, 1,1,2-trichlorotrimethyldisilane, and 1,1,3,3-tetrachlorodimethyldisilane), 6% of siloxanes of the general formula $Cl_xMe_{3-x}SiOSiMe_{3-y}Cl_y$, where each of x and y is 0–3, 17% of silamethylenes (carbosilanes) of the general formula $Cl_xMe_{3-x}SiCH_2SiMe_{3-y}Cl_y$, where each of x and y is 0–3, 16% of alkylchlorosilanes having alkyl groups larger than $CH_3$, and 19% of unidentified compounds, each at low concentration.

The high-boiling residue in liquid form was metered by way of a pump into a vertically positioned pipe of length 1800 mm and diameter 128 mm, with no internals, but incorporating a nozzle. Hydrogen chloride preheated to 750° C. was introduced into the nozzle by way of a separate line. The reaction tube was kept at a temperature of 550° C. via introduction of electrical energy. The resultant temperature profile in the gas space of the reactor was 430–600° C.

The gaseous product mixture emerging from the bottom of the tube was cooled to about −5° C. by way of a series of coolers. The condensed constituents were collected and analyzed by way of GC:
50% of methylchlorosilanes comprising:
  6% of dimethylchlorosilane
  4% of dichloromethylsilane
  12% of chlorotrimethylsilane
  7% of trichloromethylsilane
  21% of dichlorodimethylsilane
12% of alkylchlorosilanes having ethyl and propyl groups
1% of uncleaved disilanes
10% of siloxanes (as in the starting material)
12% of silamethylenes (as in the starting material)
15% of unidentified compounds After 72 hours of operation and dosage of about 150 kg high-boiling residue, the reactor was opened and assessed. Only very little solid was found on the reactor wall and in the spray injection region of the nozzle. The solid consisted of very fine particles and was dry, and could be easily removed by mechanical methods.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A continuous process for preparing alkylchlorosilanes from the residues of direct synthesis of alkylchlorosilanes, comprising reacting liquid constituents with a boiling point of at least 70° C. at 1013 hPa with hydrogen chloride, by introducing the residues at a temperature not above 200° C., and hydrogen chloride at a temperature higher than 200° C. into a reactor having a reaction temperature from 400° C. to 800° C.

2. The process of claim 1, wherein alkylchlorosilanes of the general formula $R_aH_bSiCl_{4-a-b}$ are prepared, where a is 1, 2, 3, or 4, b is 0, 1, or 2, and R is a methyl, ethyl, butyl, or propyl radical.

3. The process of claim 1, wherein di- and oligosilanes having Si—Si bonds are present in the residue and are cleaved, and wherein the amount of hydrogen chloride introduced is from 2 to 60 molar equivalents, based on moles of disilanes.

4. The process of claim 2, wherein di- and oligosilanes having Si—Si bonds are present in the residue and are cleaved, and wherein the amount of hydrogen chloride introduced is from 2 to 60 molar equivalents, based on moles of disilanes.

5. The process of claim 1, wherein the reactor is a tubular reactor.

6. The process of claim 2, wherein the reactor is a tubular reactor.

7. The process of claim 3, wherein the reactor is a tubular reactor.

8. The process of claim 1, in which the pressure in the reactor is from 1000 to 3000 hPa.

9. The process of claim 1, following reaction, excess hydrogen chloride is freed from alkylchlorosilanes formed and is returned to the reactor.

10. The process of claim 1, wherein said residue further contains solids.

* * * * *